(12) United States Patent
Rink et al.

(10) Patent No.: US 6,878,841 B2
(45) Date of Patent: Apr. 12, 2005

(54) DIETHYLOCTANDIOLDICARBAMATES AND DIETHYLOCTANDIOLDIALLOPHANATES, METHOD FOR THE PRODUCTION AND USE THEREOF

(75) Inventors: Heinz-Peter Rink, Münster (DE); Jochem Henkelmann, Mannheim (DE); Werner-Alfons Jung, Ascheberg (DE); Paul J. Harris, West Bloomfield, MI (US); Swaminathan Ramesh, Canton, MI (US)

(73) Assignee: BASF Coatings AG, Munster (DE)

( * ) Notice: Subject to any disclaimer, the term of this patent is extended or adjusted under 35 U.S.C. 154(b) by 48 days.

(21) Appl. No.: 10/182,528

(22) PCT Filed: Jan. 24, 2001

(86) PCT No.: PCT/EP01/00729
§ 371 (c)(1),
(2), (4) Date: Jul. 22, 2002

(87) PCT Pub. No.: WO01/56978
PCT Pub. Date: Aug. 9, 2001

(65) Prior Publication Data
US 2003/0023017 A1 Jan. 30, 2003

(30) Foreign Application Priority Data
Feb. 2, 2000 (DE) .......................................... 100 04 498

(51) Int. Cl.$^7$ ............................................ C07C 261/00
(52) U.S. Cl. ........................................... 560/24; 560/19
(58) Field of Search ..................................... 560/24, 19

(56) References Cited

U.S. PATENT DOCUMENTS

| | | | |
|---|---|---|---|
| 2,979,514 A | 4/1961 | O'Brien | 260/340.2 |
| 4,301,257 A | 11/1981 | Zengel et al. | 525/329 |
| 4,310,257 A * | 1/1982 | Field et al. | 400/208 |
| 4,758,632 A | 7/1988 | Parekh et al. | 525/383 |
| 5,356,669 A | 10/1994 | Rehfuss et al. | 427/407.1 |
| 5,474,811 A | 12/1995 | Rehfuss et al. | 427/407.1 |
| 5,605,965 A | 2/1997 | Rehfuss et al. | 525/100 |
| 5,964,928 A * | 10/1999 | Tomlinson | 106/14.21 |

FOREIGN PATENT DOCUMENTS

| | | | |
|---|---|---|---|
| DE | 44 32 897 | 3/1996 | ........... C08L/61/20 |
| EP | 594 068 | 10/1993 | ......... C09D/201/02 |
| EP | 594 071 | 10/1993 | ......... C09D/201/02 |
| EP | 594 142 | 10/1993 | ........... C08L/57/12 |
| EP | 850 986 | 12/1997 | ......... C08K/5/3492 |
| JP | 05229973 | * 9/1993 | |
| JP | 05229973 | * 9/1998 | |
| WO | WO94/10211 | 5/1994 | ............ C08F/8/30 |
| WO | WO94/10212 | 5/1994 | ............ C08F/8/30 |
| WO | WO94/10213 | 5/1994 | ............ C08F/8/30 |

OTHER PUBLICATIONS

Compt. Rend. (1941) vol. 212, pp. 911 to 913.*
Leon et al, ComptRend. (1941) vol. 212, p. 911–913 AN 1943:29287 Caplus.*
Leon et al, Compt. Rend. (1941) vol. 212, pp. 911 to 913 AN 1943:28287 caplus.*
English Abstract for DE44 32 897, Mar. 21, 1996.

* cited by examiner

Primary Examiner—Rita Desai
Assistant Examiner—Hector M. Reyes

(57) ABSTRACT

Positionally isomeric diethyloctanediol dicarbamates and diethyloctanediol diallophanates, processes for preparing them, and their use as synthesis building blocks and constituents of adhesives, sealing compounds, and coating materials.

13 Claims, No Drawings of Patent Application PCT/EP01/00729 filed on 24 Jan. 2001.

DIETHYLOCTANDIOLDICARBAMATES AND DIETHYLOCTANDIOLDIALLOPHANATES, METHOD FOR THE PRODUCTION AND USE THEREOF

This application is a National Phase Application of Patent Application PCT/EP01/00729 filed on 24 Jan. 2001.

The present invention relates to novel positionally isomeric diethyloctanediol dicarbamates and diethyloctanediol diallophanates. The present invention further relates to novel processes for preparing these novel compounds. The present invention additionally relates to the use of these novel compounds as synthesis building blocks and as constituents of adhesives, sealing compounds, and coating materials. Moreover, the present invention relates to novel adhesives, sealing compounds, and coating materials which comprise the novel compounds. The present invention further relates to novel adhesive films, seals, and coatings which can be produced with the aid of the novel adhesives, sealing compounds, and coating materials. The present invention relates not least to novel primed and unprimed substrates which carry the novel adhesive films, seals, and/or coatings.

The patents U.S. Pat. No. 5,474,811, U.S. Pat. No. 5,356,669, U.S. Pat. No. 5,605,965, WO 94/10211, WO 94/10212, WO 94/10213, EP-A-0 594 068, EP-A-0 594 071 and EP-A-0 594 142 disclose thermally curable coating materials which comprise binders (in this respect, cf. Römpp Lexikon Lacke und Druckfarben, Georg Thieme Verlag, Stuttgart, New York, 1998, "Binders", pages 73 and 74) containing at least one lateral and/or terminal carbamate group of the formula:

—O—(CO)—NH$_2$ and at least one crosslinking agent containing at least two functional groups which enter into crosslinking reactions with the carbamate group. These known coating compositions provide clearcoats possessing extremely high scratch and etch resistance. Crosslinking agents employed are primarily highly etherified melamine-formaldehyde resins. The crosslinking itself is acid catalyzed, with the catalysts used preferably being strong protic acids, especially sulfonic acids, which in general are blocked with amines.

Moreover, the European patent application 97122649.3-2102 discloses thermally curable coating materials comprising carbamate-functionalized (cf. the formula above) amino resins. These compounds are used as crosslinking agents for nonfunctionalized amino resins or for binders containing lateral carbamate-reactive functional groups. The coating materials likewise provide coatings having very good performance properties.

These known, nitrogen-rich coating materials frequently have a high viscosity, which is detrimental to the application and leveling of the coating materials. There is therefore a need to lower the viscosity of the coating materials without having to reduce their solids content. There is also a need to increase further the proportion of the complementary reactive functional groups, especially the proportion of the carbamate groups or similar groups, which are needed for thermal crosslinking. However, this should not involve any further increase in the hydrophilicity of the coating materials and of the coatings, so as not to reduce the already high level of acid resistance and moisture resistance.

In this context, the property of being hydrophilic refers to the constitutional property of a molecule or of a functional group to penetrate the aqueous phase or to remain therein. For further details, reference is made to Römpp, op. cit., "Hydrophilicity", "Hydrophobicity", pages 294 and 295.

It is an object of the present invention to provide novel carbamate-functional and/or allophanate-functional adhesives, sealing compounds, and coating materials which may be cured thermally, or thermally and with actinic radiation (dual cure), and which no longer have the disadvantages of the prior art but which instead, with a high solids content and a high proportion of nitrogen-containing, thermally crosslinking, complementary reactive functional groups, have a comparatively low viscosity and produce adhesives, sealing compounds, and coatings which have a high acid resistance and moisture resistance.

A further object of the present invention was to provide novel compounds which are highly suitable constituents of adhesives, sealing compounds, and coating materials that are curable thermally, or thermally and with actinic radiation.

Yet another object of the present invention was to provide novel compounds which are able to function as synthesis building blocks in high-molecular and low-molecular organic chemistry and in organometallic chemistry.

The invention accordingly provides the novel positionally isomeric diethyloctanediol dicarbamates and diethyloctanediol diallophanates, referred to comprehensively below as the "compounds of the invention".

The invention also provides novel processes for preparing the compounds of the invention, which are referred to comprehensively below as the "processes of the invention".

The invention further provides the novel adhesives, sealing compounds, and coating materials curable thermally, or thermally and with actinic radiation, which comprise the compounds of the invention and/or the compounds of the invention prepared with the aid of the processes of the invention and which are referred to below as the "adhesives, sealing compounds or coating materials of the invention".

Furthermore, the invention provides the novel adhesive films, seals, and coatings which can be produced from the adhesives, sealing compounds or coating materials of the invention and which are referred to below as the "adhesive films, seals or coatings of the invention".

Further subject-matter of the invention will emerge from the following description.

In the light of the prior art it was surprising for the skilled worker that the object on which the present invention is based might be achieved with the aid of the compounds of the invention. A particular surprise in this context was the ready availability of the compounds of the invention and their extremely broad usefulness.

The compounds of the invention contain primary, secondary or tertiary carbamate groups or allophanate groups. In light of the use in the adhesives, sealing compounds, and coating materials of the invention, the primary and secondary carbamate groups and allophanate groups are of advantage and are therefore used with preference. Particular advantages, however, are afforded by primary carbamate groups and allophanate groups, which accordingly are used with particular preference in accordance with the invention.

The compounds of the invention contain a linear C8 carbon chain.

With regard to the two ethyl groups, the linear C8 carbon chain has the following substitution pattern: 2,3, 2,4, 2,5, 2,6, 2,7, 3,4, 3,5, 3,6 or 4,5. In accordance with the invention it is of advantage if the two ethyl groups are in positions 2 and 4, i.e., if the compounds are 2,4-diethyloctanediol dicarbamates and 2,4-diethyloctanediol diallophanates.

With regard to the two hydroxyl groups, the C8 carbon chain has the following substitution pattern: 1,2, 1,3, 1,4, 1,5, 1,6, 1,7, 1,8, 2,3, 2,4, 2,5, 2,6, 2,7, 2,8, 3,4, 3,5, 3,6, 3,7, 3,8, 4,5, 4,6, 4,8, 5,6, 5,7, 5,8, 6,7, 6,8 or 7,8. In accordance with the invention it is of advantage if the two hydroxyl groups are in positions 1 and 5, i.e., if the compounds are diethyloctane-1,5-diol dicarbamates or diethyloctane-1,5-diol diallophanates.

The two substitution patterns are combined with one another in any desired way; i.e., the compounds of the invention comprise 2,3-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
2,4-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
2,5-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
2,6-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
2,7-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
3,4-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
3,5-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
3,6-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol, or
4,5-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol dicarbamates or diallophanates.

Of these compounds of the invention, 2,4-diethyloctane-1,5-diol dicarbamate and 2,4-diethyloctane-1,5-diol diallophanate, but especially 2,4-diethyloctane-1,5-diol dicarbamate, have particular advantages in the context of their preparation and of their use, and so are used with particular preference in accordance with the invention.

The preparation of the compounds of the invention starts from the positionally isomeric diethyloctanediols.

The positionally isomeric diethyloctanediols for use in accordance with the invention contain a linear C8 carbon chain whose substitution pattern determines the substitution pattern of the compounds of the invention.

With regard to the two ethyl groups, the linear C8 carbon chain has the following substitution pattern: 2,3, 2,4, 2,5, 2,6, 2,7, 3,4, 3,5, 3,6 or 4,5. In accordance with the invention it is of advantage if the two ethyl groups are in positions 2 and 4, i.e., if the compounds are 2,4-diethyloctanediols.

With regard to the two hydroxyl groups, the C8 carbon chain has the following substitution pattern: 1,2, 1,3, 1,4, 1,5, 1,6, 1,7, 1,8, 2,3, 2,4, 2,5, 2,6, 2,7, 2,8, 3,4, 3,5, 3,6, 3,7, 3,8, 4,5, 4,6, 4,8, 5,6, 5,7, 5,8, 6,7, 6,8 or 7,8. In accordance with the invention it is of advantage if the two hydroxyl groups are in positions 1 and 5, i.e., if the compounds are diethyloctane-1,5-diols.

The two substitution patterns are combined with one another in any desired way; i.e., the diethyloctanediols to be used in accordance with the invention comprise 2,3-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
2,4-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
2,5-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
2,6-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
2,7-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3, 8-, -4,5-, -4,6-, -4,7-, -4,8-, -5,6-, -5,7-, -5,8-, -6,7-, -6,8- or -7,8-diol,
3,4-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
3,5-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol,
3,6-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol, or
4,5-diethyloctane-1,2-, -1,3-, -1,4-, -1,5-, -1,6-, -1,7-, -1,8-, -2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- or -7,8-diol.

Particular advantages result from the use of 2,4-diethyloctane-1,5-diol.

The positionally isomeric diethyloctanediols for use in accordance with the invention are compounds which are known per se and they can be prepared with the aid of customary and known synthesis methods of organic chemistry such as base-catalyzed aldol condensation or are obtained as by-products of large-scale chemical syntheses such as the preparation of 2-ethylhexanol.

The compounds of the invention may be prepared in any desired, appropriate way in accordance with the customary and known methods of organic chemistry, especially of organic nitrogen chemistry. In accordance with the invention, however, it is of advantage to prepare them in accordance with the processes of the invention.

The first process of the invention for preparing the positionally isomeric diethyloctanediol dicarbamates of the invention comprises the reaction of the above-described positionally isomeric diethyloctanediols with alkyl, cycloalkyl or aryl carbamates, especially methyl, butyl, cyclohexyl or phenyl carbamate, to give the positionally isomeric diethyloctanediol dicarbamates of the invention plus alcohols or phenols as by-products. The by-products may be separated off in a customary and known manner, by distillation, for example. Viewed in terms of its method, the process of the invention has no special features but instead is carried out along the lines of the methods and conditions described in the patents U.S. Pat. Nos. 4,758,632, 4,301,257 and 2,979,514.

The second process of the invention for preparing the positionally isomeric diethyloctanediol dicarbamates of the invention comprises the reaction of positionally isomeric diethyloctanediols with phosgene to give the corresponding positionally isomeric chloroformates.

Viewed in terms of its method, the preparation of the chloroformate-functional intermediates has no special features but instead takes place in accordance with the customary and known methods of phosgene chemistry, using the corresponding suitable equipment and taking the safety measures which are customary for the handling of phosgene.

Advantageously, the reaction with phosgene is conducted at temperatures of from −10 to 100, preferably from 0 to 50, and in particular from 10 to 40° C., depending on the reactivity of the diethyloctanediols and/or on the stirability of the particular solution of the diethyloctanediols.

Although the chloroformate-functional intermediates may be isolated as such, which may very well be of advantage for specific cases, it is generally advisable to react the intermediates in the solution in which they are produced with ammonia and/or primary and/or secondary amines.

Examples of suitable primary and secondary amines are those of the general formula I

in which the variable R represents a hydrogen atom or represents monovalent organic radical derived from the following compounds:
(i) substituted and unsubstituted, linear or branched alkanes, alkenes, cycloalkanes, cycloalkenes, alkylcycloalkanes, alkylcycloalkenes, alkenylcycloalkanes or alkenylcycloalkenes containing no or at least one heteroatom in the chain and/or in the ring;
(ii) substituted and unsubstituted aromatics or heteroaromatics; and also
(iii) alkyl-, alkenyl-, cycloalkyl-, cycloalkenyl-, alkylcycloalkyl-, alkylcycloalkenyl-, alkenylcycloalkyl- or alkenylcycloalkenyl-substituted aromatics or heteroaromatics whose substituents are substituted or unsubstituted and contain no or at least one heteroatom in their chain and/or their ring;
and in which the variable $R^1$ has the meaning indicated above with the exception of a hydrogen atom;
or in which the radicals R, with the exception of a hydrogen atom, and $R^1$ are linked cyclically with one another.

Examples of suitable heteroatoms are oxygen, nitrogen, boron, silicon, sulfur, and phosphorus atoms.

Examples of suitable substituents for the abovementioned radicals $R^1$ are halogen atoms, especially fluorine and chlorine atoms, nitro groups, and nitrile groups.

Examples of suitable aromatics are benzene and naphthalene.

Examples of suitable heteroaromatics are thiophene, pyridine, and triazine.

Examples of suitable alkanes are those having 1 to 20 carbon atoms in the molecule such as methane, ethane, propane, butane, isobutane, pentane, neopentane, hexane, heptane, octane, isooctane, nonane, dodecane, hexadecane or eicosane.

Examples of suitable alkenes are ethylene and propylene.

Examples of suitable cycloalkanes are cyclopentane and cyclohexane.

Examples of suitable cycloalkenes are cyclopentene and cyclohexene.

Examples of suitable alkylcycloalkanes are methylcyclopentane and methylcyclohexane.

Examples of suitable alkylcycloalkenes are methylcyclopentene and methylcyclohexene.

Examples of suitable alkenylcycloalkanes are allyl- and vinylcyclopentane and allyl- and vinylcyclohexane.

Examples of suitable alkenylcycloalkenes are vinylcyclopentene and vinylcyclohexene.

Examples of suitable alkyl, alkenyl, cycloalkyl, cycloalkenyl, alkylcycloalkyl, alkylcycloalkenyl, alkenylcycloalkyl and alkenylcycloalkenyl substituents are methyl, ethyl, propyl, isopropyl, n-butyl, sec-butyl, tert-butyl, vinyl, allyl, cyclohexyl, cyclohexenyl, 4-methylcyclohexyl, 4-methylcyclohexenyl, 3-allylcyclohexenyl, and 4-vinylcyclohexenyl.

The radicals $R^1$ are preferably derived from organic compounds which are unsubstituted per se or whose substituents are unsubstituted.

Advantageously, these compounds also contain no heteroatoms in their chains and/or in their rings and/or in the chains and/or the rings of their substituents.

Particular advantages result if the radicals R and $R^1$ are derived from linear alkanes which meet the abovementioned advantageous conditions. Further advantages result if they are derived from methane, ethane, propane, butane, pentane or hexane.

Examples of highly suitable primary amines I are methylamine, ethylamine, propylamine, isobutylamine, hexylamine, cyclohexylamine, allylamine, cyclohexenylamine, aniline, cyclohexylmethylamine, (2-cyclohexyl)ethylamine and benzylamine.

Reaction with these primary amines I results in diethyloctanediol dicarbamates of the invention containing secondary carbamate groups.

Examples of highly suitable secondary amines I are dimethylamine, diethylamine, methylethylamine, dicyclohexylamine, methylcyclohexylamine, dibenzylamine, methylbenzylamine and diphenylamine.

Examples of highly suitable cyclic amines I are imidazole, thiazine, morpholine, and piperidine.

Reaction with these secondary amines I results in diethyloctanediol dicarbamates of the invention containing tertiary carbamate groups.

Particular advantages result if the radicals R and $R^1$ are derived from linear alkanes which meet the abovementioned advantageous conditions. Further advantages result if they are derived from methane, ethane, propane, butane, pentane or hexane.

Examples of highly suitable primary amines I are methylamine, ethylamine, propylamine, isobutylamine, hexylamine, cyclohexylamine, allylamine, cyclohexenylamine, aniline, cyclohexylmethylamine, (2-cyclohexyl)-ethylamine and benzylamine.

Reaction with these primary amines I results in diethyloctanediol dicarbamates of the invention containing secondary carbamate groups.

Examples of highly suitable secondary amines I are dimethylamine, diethylamine, methylethylamine, dicyclohexylamine, methycyclohexylamine, dibenzylamine, methylbenzylamine and diphenylamine.

Examples of highly suitable cyclic amines I are imidazole, thiazine, morpholine, and piperidine.

Reaction with these secondary amines I results in diethyloctanediol dicarbamates of the invention containing tertiary carbamate groups.

Since diethyloctanediol dicarbamates of the invention which contain primary carbamate groups are very particularly advantageous, ammonia is used with very particular preference in accordance with the invention.

Viewed in terms of method, the reaction of ammonia and/or of amines I with the chloroformate-functional intermediates has no special features but instead takes place in accordance with the customary and known methods of organic chemistry. The equipment and techniques used for this purpose are guided in particular by whether solid, liquid or gaseous amines I or gaseous or dissolved ammonia are or is used. The skilled worker will therefore be able to select the appropriate techniques and equipment in a simple manner on the basis of his or her knowledge in the art.

The ammonium chlorides which are produced in the reaction of the chloroformate groups with ammonia or with the amines I are separated from the reaction mixture, comprising the diethyloctanediol dicarbamate of the invention, in a customary and known manner. Examples of suitable methods are filtration or extraction, it being possible to combine these methods with one another in an appropriate way.

The process of the invention for preparing the positionally isomeric diethyloctanediol allophanates of the invention comprises the reaction of the positionally isomeric diethyloctanediols with alkyl, cycloalkyl or aryl allophanates, especially alkyl allophanates, particularly methyl or ethyl allophanate. In accordance with the invention it is of advantage to conduct the reaction at from 50 to 150° C., preferably from 60 to 130° C., and in particular from 80 to 120° C. A particularly good reaction course is ensured if the alcohol and/or phenol are/is removed continually from the reaction mixture, by distillation in vacuo, for example. In order to accelerate the reaction, a customary and known acidic catalyst such as p-toluene-sulfonic acid may also be added to the reaction mixture.

Depending on the intended use, the compounds of the invention may be isolated following their preparation and prior to their use, or else the solutions in which they are obtained may be used directly. The preferred variant is guided in particular by the intended use. For instance, in the context of their use in solventborne adhesives, sealing compounds, and coating materials, the diethyloctanediol dicarbamates of the invention will be employed in solution, whereas prior to their use in solvent-free solid or liquid adhesives, sealing compounds and coating materials they are isolated.

Because of their new kinds of structure, the compounds of the invention may be used as valuable synthesis building blocks in low-molecular and high-molecular organic chemistry and in organometallic chemistry.

The compounds of the invention may further be used for the preparation of adhesives, sealing compounds, and coating materials curable thermally and/or with actinic radiation. In particular, they are employed as constituents of the adhesives, sealing compounds, and coating materials of the invention. In this context, their proportion in the adhesives, sealing compounds, and coating materials of the invention may vary extremely widely. Where the compounds of the invention constitute the principal constituent of the adhesives, sealing compounds, and coating materials of the invention, their proportion therein may preferably be up to 95, more preferably 90, with particular preference 85, with very particular preference 80, and in particular 75% by weight, based in each case on the adhesives, sealing compounds or coating materials of the invention. Alternatively, the compounds of the invention may be employed as additives in the function of reactive diluents (in this regard, cf. Römpp, op. cit., "Reactive diluents", p. 491) for the thermal crosslinking. In this case, just a proportion of preferably from 0.1 to 20, more preferably from 0.2 to 18, with particular preference from 0.3 to 16, with very particular preference from 0.4 to 14, and in particular from 0.5 to 12% by weight, based in each case on the adhesives, sealing compounds or coating materials of the invention, is sufficient to achieve the advantages of the invention.

The adhesives, sealing compounds or coating materials of the invention may further comprise customary and known binders, crosslinking agents, and additives in effective amounts.

The binders may come from any of a very wide variety of oligomer and polymer classes. Examples of suitable oligomer and polymer classes are random, alternating and/or block, linear and/or branched and/or comb addition (co) polymers of ethylenically unsaturated monomers, or polyaddition resins and/or polycondensation resins. Regarding these terms, reference is made for further details to Römpp, op. cit., page 457, "Polyaddition" and "Polyaddition resins (polyadducts)", and also pages 463 and 464, "Polycondensates", "Polycondensation", and "Polycondensation resins". As regards any substituents which may be present, the remarks made above apply accordingly.

Examples of highly suitable addition (co)polymers are poly(meth)acrylates and partially saponified polyvinyl esters.

Examples of highly suitable polyaddition resins and/or polycondensation resins are polyesters, alkyds, polyurethanes, polylactones, polycarbonates, polyethers, epoxy resin-amine adducts, polyureas, polyamides, and polyimides.

Particular advantages result if the above-described binders contain carbamate-reactive functional groups such as N-methylol or N-methylol ether groups.

Examples of suitable crosslinking agents are amino resins. Examples of suitable amino resins are customary and known, and numerous products are available commercially.

Examples of highly suitable amino resins are melamine resins, guanamine resins, and urea resins. In this context it is possible to use any amino resin suitable for transparent topcoats or clearcoats, or a mixture of such amino resins. For further details, reference is made to Römpp, op. cit., page 29, "Amino resins", and the textbook "Lackadditive" [Additives for coatings] by Johan Bieleman, Wiley-VCH, Weinheim, N.Y., 1998, pages 242 ff., or to the book "Paints, Coatings and Solvents", second, completely revised edition, edited by D. Stoye and W. Freitag, Wiley-VCH, Weinheim, N.Y., 1998, pages 80 ff. Also suitable are the customary and known amino resins some of whose methylol and/or methoxymethyl groups have been defunctionalized by means of carbamate or allophanate groups. Crosslinking agents of this kind are described in the patents U.S. Pat. No. 4,710,542 and EP-B-0 245 700 and also in the article by B. Singh and coworkers, "Carbamylmethylated melamines, novel crosslinkers for the coatings industry" in Advanced Organic Coatings Science and Technology Series, 1991, volume 13, pages 193 to 207.

Besides these crosslinking agents, further crosslinking agents may also be present. Examples of suitable further crosslinking agents are resins or compounds containing siloxane groups, resins or compounds containing anhydride groups, resins or compounds containing epoxide groups, blocked and/or unblocked polyisocyanates, and/or tris (alkoxycarbonylamino)-triazines, as described in the patents U.S. Pat. No. 4,939,213, U.S. Pat. No. 5,084,541, U.S. Pat. No. 5,288,865 and EP-A-0 604 922.

Depending on the reactivity of the further crosslinking agent, it may be added directly to the coating materials, adhesives, and sealing compounds of the invention to give what is known as a one-component system. If, however, it is a particularly reactive crosslinking agent, such as a polyisocyanate or an epoxide, it is generally not added to the coating materials, adhesives, and sealing compounds of the invention until shortly before use. The result in this case is what is known as a two-component or multicomponent system.

Where the coating materials, adhesives, and sealing compounds of the invention are to be curable not only thermally but also with actinic radiation, they include customary and known constituents which can be activated with actinic radiation. In the context of the present invention actinic radiation means electromagnetic radiation, especially visible light, UV light or X-rays, or corpuscular radiation, especially electron beams. The use of UV light is particularly preferred. Examples of suitable constituents which can be activated with actinic radiation are (meth)acryloyl-, allyl-, vinyl- or dicyclopentadienyl-functional (meth)acrylic copolymers or polyether acrylates, polyester acrylates, unsaturated polyester acrylates, epoxy acrylates, urethane acrylates, amino acrylates, melamine acrylates, silicone acrylates, or the corresponding methacrylates.

Examples of suitable additives are crosslinking catalysts, initiators, in particular photoinitiators, pigments, dyes, fillers, reinforcing fillers, Theological aids, solvents, wetting agents, dispersants, defoamers, adhesion promoters, additives for improving substrate wetting, additives for improving surface smoothness, flatting agents, leveling agents, film-forming auxiliaries, dryers, antiskinning agents, light stabilizers, corrosion inhibitors, biocides, flame retardents, polymerization inhibitors, especially photoinhibitors, or plasticizers, as customary and known, for example, in the plastics or coatings sector. Further examples of suitable additives (C) are described in the textbook "Lackadditive" by Johan Bieleman, Wiley-VCH, Wienheim, N.Y., 1998.

The selection of the additives is guided by the desired profile of properties of the coating compositions, adhesives, and sealing compounds of the invention and by their specific end uses and may therefore be made by the skilled worker in a simple manner, possibly with the assistance of simple preliminary tests.

The adhesives, sealing compounds, and coating materials of the invention may be present in dispersion or solution in aqueous, aqueous-organic or organic media or may be present as a so-called NAD (non-aqueous dispersion). Furthermore, they may be present in fine division in solid form, as powder coating materials, for example, or in solid forms dispersed in water, as powder slurries, for example. Moreover, they may be present in solvent-free liquid form, as what are known as 100% systems. The constituents of the adhesives, sealing compounds, and coating materials of the invention that are required in each case are easy for the skilled worker to select on the basis of the given profile of properties (solid, liquid, soluble in organic solvents, water-soluble, etc.).

The preparation of the adhesives, sealing compounds, and coating materials of the invention has no special features but instead takes place in a customary and known manner by mixing of the above-described constituents in suitable mixing equipment such as stirred vessels, dissolvers, stirred mills, or extruders in accordance with the methods suitable for the preparation of the respective adhesives, sealing compounds, and coating materials of the invention.

The adhesives of the invention are used to produce adhesive films of the invention on primed and unprimed substrates.

The sealing compounds of the invention are used to produce seals of the invention on and in primed and unprimed substrates.

The coating materials of the invention may be used as primer-surfacers, solid-color topcoat materials, basecoat materials, and clearcoat materials and are used to produce single-coat or multicoat clearcoat systems or color and/or effect coating sytems on primed and unprimed substrates.

Very particular advantages result in the context of their use to produce clearcoat systems, especially in the context of what is known as the wet-on-wet technique, in which a basecoat material, in particular an aqueous basecoat material, is applied to the primed or unprimed substrate and dried but not cured, after which a clearcoat material is applied to the basecoat film and the resultant clearcoat film is cured together with the basecoat film, thermally, or thermally and with actinic radiation.

Suitable coating substrates are all surfaces which are not damaged by curing of the films present thereon using heat or a combination of heat and actinic radiation; examples of such substrates include metals, plastics, wood, ceramic, stone, textile, fiber composites, leather, glass, glass fibers, glass wool, rock wool, mineral-bound and resin-bound building materials, such as plasterboard, cement slabs or roof tiles, and composites of these materials. Accordingly, the coatings, adhesive films or seals of the invention are also suitable for applications outside of automotive OEM finishing and automotive refinish. Here they are particularly suitable for the coating, bonding and/or sealing of furniture and for industrial application, including coil coating, container coating, and the impregnation or coating of electrical components. In the context of the industrial applications, they are suitable for coating, bonding and/or sealing virtually all parts for private or industrial use, such as radiators, domestic applicances, small metal parts such as nuts and bolts, hubcaps, wheel rims, packaging, or electrical components such as motor windings or transformer windings.

In the case of electrically conductive substrates it is possible to use primers, which are produced in a customary and known manner from electrodeposition coating materials. For this purpose both anodic and cathodic electrodeposition coating materials are suitable, but especially cathodic electrocoats.

It is also possible to coat, bond or seal primed or unprimed plastics parts made, for example, of ABS, AMMA, ASA, CA, CAB, EP, UF, CF, MF, MPF, PF, PAN, PA, PE, HDPE, LDPE, LLDPE, UHMWPE, PC, PC/PBT, PC/PA, PET, PMMA, PP, PS, SB, PUR, PVC, RF, SAN, PBT, PPE, POM, PUR-RIM, SMC, BMC, PP-EDPM, and UP (abbreviations in accordance with DIN 7728T1). Nonfunctionalized and/or nonpolar substrate surfaces may be subjected prior to coating in a known manner to a pretreatment, such as with a plasma or by flaming, or may be provided with a water-based primer.

The application of the adhesives, sealing compounds, and coating materials of the invention may take place by any customary application method, such as spraying, knife coating, brushing, flow coating, dipping, impregnating, trickling or rolling, for example. The substrate to be coated may itself be at rest, with the application equipment being moved. Alternatively, the substrate to be coated, especially a coil, may be moved, with the application unit being at rest relative to the substrate or being moved appropriately. Where the adhesives, sealing compounds, and coating materials of the invention include constituents which can be activated with actinic radiation, the application is preferably carried out in the absence of light.

The applied films of the adhesives, sealing compounds, and coating materials of the invention are cured thermally, or thermally and with actinic radiation, in a customary and known manner, after allowing if desired a certain rest period which is used for leveling of the films and/or for the evaporation of volatile constituents.

In terms of its method, the thermal curing has no special features but instead the customary and known temperatures in the range from room temperature up to 200° C., curing times in the range from one minute to three hours, and equipment such as radiant heaters or forced-air ovens, are employed.

Curing with actinic radiation also has no special features in terms of its method but instead takes place in a customary and known manner by irradiation with UV lamps and/or electron beam sources, preferably under inert gas.

In the context of the curing of the dual-cured adhesives, sealing compounds, and coating materials of the invention, the thermal curing and curing with actinic radiation may be employed simultaneously or alternately. Where the two curing methods are used alternately, it is possible, for example, to commence with thermal curing and to end with curing-with actinic radiation. In other cases it may prove advantageous to commence with curing with actinic radiation and to end with it as well. The skilled worker is able to determine the curing method most advantageous for the case in hand on the basis of his or her general knowledge in the art, possibly with the assistance of simple preliminary tests.

The adhesive films and seals of the invention produced from the adhesives and sealing compounds of the invention possess outstanding bond strength and sealing capacity, even under extreme climatic conditions and over long periods of time.

The coatings of the invention produced from the coating materials of the invention exhibit excellent leveling and have an outstanding overall appearance. They are weathering-stable, acid-resistant and moisture-resistant, and do not yellow even under tropical conditions. They can therefore be used both inside and outside.

Accordingly, the primed and unprimed substrates of the invention, especially bodies of automobiles and commercial vehicles, industrial components, including plastics parts, packaging, coils and electrical components, or furniture, which have been coated with at least one coating of the invention, sealed with at least one seal of the invention and/or bonded with at least one adhesive of the invention feature particular technical and economic advantages, in particular a long service life, so making them particularly attractive to users.

EXAMPLES

Example 1

Preparation of 2,4-diethyloctane-1,5-diol dicarbamate

A 2 l glass apparatus with gas inlet tube, a brine condenser (−15° C.) and a dry-ice condenser was charged with 50 g of toluene and this initial charge was saturated with phosgene at from 50 to 55° C. until a phosgene reflux set in. Thereafter, 4 g (2 mol) of 2,4-diethyl-1,5-octanediol (hydroxyl number 536 mg KOH/g) in solution in 808 g of toluene were reacted with a total of 480 g of phosgene at from 50 to 55° C. over the course of 4 hours. Following a post-reaction period of 30 minutes at from 50 to 55° C., the reaction mixture was stripped free of phosgene using nitrogen.

Subsequently, at from room temperature to 40° C., a total of 155 g of gaseous ammonia was passed in over the course of 2.5 hours, forming a white precipitate of ammonium chloride. After the end of reaction, at 70° C., 400 ml of water were added in order to separate off the ammonium chloride. The aqueous phase was separated off at 70° C. and the organic phase was washed with twice 400 ml of water at 70° C. Subsequently, the organic phase was concentrated on a rotary evaporator.

This gave 558 g (96.8%) of 2,4-diethyl-1,5-octanediol dicarbamate having a hydroxyl number of 27 mg KOH/g. The IR spectrum showed the carbamate band as sole functional group.

Preparation Example 1

The Preparation of a Binder for Use in a Clearcoat Material of the Invention

An appropriate reaction vessel equipped with stirrer, reflux condenser and two feed vessels was charged with 100 parts by weight of a mixture of 2,4-diethyloctane-1,5-diol, methyl amyl ketone and ethoxyethyl propionate (weight ratio: 1:1:1) and this initial charge was heated to 145° C. A mixture of 100 parts by weight of VeoVa® 10 (cf. Römpp, op. cit., "VeoVa®", page 598), 150 parts by weight of styrene, 100 parts by weight of tert-butylcyclohexyl acrylate, 200 parts by weight of n-butyl methacrylate, 10 parts by weight of 2-hydroxyethyl acrylate and 100 parts by weight of isodecyl methacrylate was metered into the initial charge at a uniform rate over the course of 4.5 hours with stirring. 15 minutes before the beginning of this feed stream, the addition of a mixture of 40 parts by weight of di-tert-butyl peroxide and methyl amyl ketone was commenced. This mixture was metered into the resulting reaction mixture at a uniform rate over 5 hours. Following postpolymerization, the reaction mixture was adjusted using methoxypropyl acetate to a solids content of 74% by weight (one hour at 130° C.).

Example 2

Preparation and Application of a Clearcoat Material of the Invention 1 part by weight of 2,4-diethyloctane-1,5-diol dicarbamate (cf. example 1), 1 part by weight of a commercial melamine resin (Luwipal® 066 from BASF Aktiengesellschaft), 121.62 parts by weight of the binder solution from preparation example 1 and 0.28 part by weight of a commercial acidic crosslinking catalyst (Nacure® 4575) were mixed with one another. The resulting clearcoat material was applied to glass in a wet film thickness of 100 µm and was cured at 130° C. for 30 minutes. The resulting clearcoat of the invention was clear, transparent, scratch-resistant and acid-resistant.

What is claimed is:

1. A composition comprising a positionally isomeric diethyloctanediol dicarbamate, a positionally isomeric diethyloctanediol diallophanate, or a positionally isomeric diethyloctanediol dicarbamate and a positionally isomeric diethyloctanediol diallophanate.

2. The composition of claim 1, wherein at least one of i) the positionally isomeric diethyloctanediol dicarbamate contains a primary carbamate group, and ii) the positionally isomeric diethyloctanediol diallophanate contains a primary allophanate group.

3. The composition of claim 1, wherein at least one of i) the ethyl groups on the linear octane of the positionally isomeric diethyloctanediol dicarbamate have a substitution pattern, with regard to the two ethyl groups, that is one of 2,3; 2,4; 2,5; 2,6; 2,7; 3,4; 3,5; 3,6; and 4,5; and ii) the ethyl groups on the linear octane of the positionally isomeric diethyloctanediol diallophanate have a substitution pattern, with regard to the two ethyl groups, that is one of 2,3; 2,4; 2,5; 2,6; 2,7; 3,4; 3,5; 3,6; and 4,5.

4. The composition of claim 3, wherein the two ethyl groups are in positions 2 and 4.

5. The composition of claim 1, wherein at least one of i) the carbamate groups on the linear octane of the positionally isomeric diethyloctanediol dicarbamate have a substitution pattern, with regard to the two carbamate groups, that is one of 1,2; 1,3; 1,4; 1,5; 1,6; 1,7; 1,8; 2,3; 2,4; 2,5; 2,6; 2,7; 2,8; 3,4; 3,5; 3,6; 3,7; 3,8; 4,5; 4,6; 4,8; 5,6; 5,7; 5,8; 6,7; 6,8; and 7,8, and ii) the allophanate groups of the positionally isomeric diethyloctanediol diallophanate have a substitution pattern, with regard to the two allophanate groups, that is one of 1,2; 1,3; 1,4; 1,5; 1,6; 1,7; 1,8; 2,3; 2,4; 2,5; 2,6; 2,7; 2,8; 3,4; 3,5; 3,6; 3,7; 3,8; 4,5; 4,6; 4,8; 5,6; 5,7; 5,8; 6,7; 6,8; and 7,8.

6. The composition of claim 5, wherein at least one of i) the two carbamate groups are in positions 1 and 5, and ii) the two allophanate groups are in positions 1 and 5.

7. The composition of claim 6, wherein at least one of i) the positionally isomeric diethyloctanediol dicarbamate is 2,4-diethyloctane-1,5-diol dicarbamate, and ii) the positionally isomeric diethyloctanediol diallophanate is 2,4-diethyloctane-1,5-diol diallophanate.

8. The composition of claim 1, wherein at least one of i) the hydroxyl groups on the linear octane of the positionally isomoric diethyloctanediol dicarbamate have a substitution pattern, with regard to the two hydroxyl groups, that is one of 1,2; 1,3; 1,4; 1,5; 1,6; 1,7; 1,8; 2,3; 2,4; 2,5; 2,6; 2,7; 2,8; 3,4; 3,5; 3,6; 3,7; 3,8; 4,5; 4,6; 4,8; 5,6; 5,7; 5,8; 6,7; 6,8; and 7,8, and ii) the hydroxyl groups on the linear octane of the positionally isomeric diethyloctanediol diallophanate have a substitution pattern, with regard to the two hydroxyl groups, that is one of 1,2; 1,3; 14; 1,5; 1,6; 1,7; 1,8; 2,3; 2,4; 2,5; 2,6; 2,7; 2,8; 3,4; 3,5; 3,6; 3,7; 3,8; 4,5; 4,6; 4,8; 5,6; 5,7; 5,8; 6,7; 6,8; and 7,8.

9. The composition of claim 8, wherein the two hydroxyl groups are in positions 1 and 5.

10. A method comprising reacting the positionally isomeric diethyloctanediol dicarbamate, the positionally isomeric diethyloctanediol diallophanate, or the positionally isomeric diethyloctanediol dicarbamate and the positionally isomeric diethyloctanediol diallophanate of claim 1 to form a reaction product.

11. The reaction product produced by the method of claim 10, wherein the reaction product is one of an adhesive, a sealing compound, a coating material, wherein the coating material is curable by one of i) thermally and ii) thermally and with actinic radiation.

12. A composition formed from the reaction product of claim 11, wherein the composition is one of an adhesive film, a seal, and a coating.

13. A substrate comprising the composition of claim 12, wherein the substrate is one of primed and unprimed.

* * * * *